US008992592B2

(12) United States Patent
Molaei et al.

(10) Patent No.: US 8,992,592 B2
(45) Date of Patent: Mar. 31, 2015

(54) MEDICAL DEVICES INCLUDING METALLIC FILMS

(75) Inventors: Masoud Molaei, Fremont, CA (US); John Peckham, Sunnyvale, CA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 539 days.

(21) Appl. No.: 11/025,464

(22) Filed: Dec. 29, 2004

(65) Prior Publication Data

US 2006/0142851 A1    Jun. 29, 2006

(51) Int. Cl.
*A61F 2/06* (2013.01)
*A61F 2/90* (2013.01)
*A61F 2/07* (2013.01)
*A61F 2/91* (2013.01)
*A61F 2/915* (2013.01)
*A61F 2/95* (2013.01)
*A61F 2/30* (2006.01)
*A61F 2/82* (2013.01)

(52) U.S. Cl.
CPC ... *A61F 2/90* (2013.01); *A61F 2/07* (2013.01); *A61F 2/91* (2013.01); *A61F 2/915* (2013.01); *A61F 2/95* (2013.01); *A61F 2002/075* (2013.01); *A61F 2002/30329* (2013.01); *A61F 2002/823* (2013.01); *A61F 2002/91525* (2013.01); *A61F 2002/91533* (2013.01); *A61F 2002/91575* (2013.01); *A61F 2220/0025* (2013.01); *A61F 2230/0013* (2013.01); *A61F 2210/0076* (2013.01); *A61F 2220/0041* (2013.01); *A61F 2220/005* (2013.01); *A61F 2220/0058* (2013.01); *A61F 2230/0054* (2013.01)
USPC ......................................................... 623/1.13

(58) Field of Classification Search
USPC ........... 623/1.13, 1.15, 1.34, 1.42, 1.44–1.46, 623/1.14
See application file for complete search history.

(56) References Cited

U.S. PATENT DOCUMENTS

| 4,793,348 | A | 12/1988 | Palmaz |
| 4,864,824 | A | 9/1989 | Gabriel et al. |
| 5,035,706 | A | 7/1991 | Giantureo et al. |

(Continued)

FOREIGN PATENT DOCUMENTS

| EP | 0472731 | 8/1991 |
| EP | 0 792 627 A2 | 9/1997 |

(Continued)

OTHER PUBLICATIONS

International Search Report for PCT Application No. PCT/US2005/007162.

(Continued)

*Primary Examiner* — Gregory Anderson
(74) *Attorney, Agent, or Firm* — Kacvinsky Daisak Bluni PLLC

(57) ABSTRACT

An endoprosthesis for deployment within a body passage includes an external tubular framework disposed about a tubular member, e.g., a metallic film having a thickness of about 50 µm or less. The tubular member may be sandwiched between the external tubular framework and an internal tubular framework located internally of the external tubular framework and the tubular member. Whether or not the internal tubular framework is included, the endoprosthesis can be self-expanding. During deployment of the endoprosthesis using a deployment device, the external tubular framework prevents substantial frictional contact between the deployment device and the tubular member.

20 Claims, 6 Drawing Sheets

(56) References Cited

U.S. PATENT DOCUMENTS

| | | | |
|---|---|---|---|
| 5,061,914 A | 10/1991 | Busch et al. | |
| 5,085,535 A | 2/1992 | Solberg et al. | |
| 5,119,555 A | 6/1992 | Johnson | |
| 5,245,738 A | 9/1993 | Johnson | |
| 5,302,261 A | 4/1994 | LeRoy et al. | |
| 5,306,294 A | 4/1994 | Winston et al. | |
| 5,325,880 A | 7/1994 | Johnson et al. | |
| 5,382,261 A | 1/1995 | Palmaz | |
| 5,405,378 A | 4/1995 | Strecker et al. | |
| 5,441,515 A | 8/1995 | Khosravi et al. | |
| 5,518,680 A | 5/1996 | Cima et al. | |
| 5,554,182 A | 9/1996 | Dinh et al. | |
| 5,556,413 A | 9/1996 | Lam | |
| 5,607,466 A | 3/1997 | Imbert et al. | |
| 5,619,177 A | 4/1997 | Johnson et al. | |
| 5,656,036 A | 8/1997 | Palmaz | |
| 5,667,523 A | 9/1997 | Bynon et al. | |
| 5,674,242 A | 10/1997 | Phan et al. | |
| 5,676,697 A | 10/1997 | McDonald | |
| 5,728,150 A | 3/1998 | McDonald et al. | |
| 5,755,734 A | 5/1998 | Richter et al. | |
| 5,800,517 A | 9/1998 | Anderson et al. | |
| 5,817,102 A | 10/1998 | Johnson et al. | |
| 5,824,042 A | 10/1998 | Lombardi et al. | |
| 5,824,049 A | 10/1998 | Ragheb et al. | |
| 5,824,054 A | 10/1998 | Khosravi et al. | |
| RE35,988 E | 12/1998 | Winston et al. | |
| 5,843,158 A | 12/1998 | Lenker et al. | |
| 5,843,164 A | 12/1998 | Frantzen et al. | |
| 5,843,289 A | 12/1998 | Lee et al. | |
| 5,849,206 A | 12/1998 | Amon et al. | |
| 5,860,998 A | 1/1999 | Robinson et al. | |
| 5,865,723 A | 2/1999 | Love et al. | |
| 5,882,444 A | 3/1999 | Flomenblit et al. | |
| 5,888,734 A | 3/1999 | Cremer et al. | |
| 5,897,911 A | 4/1999 | Loeffler | |
| 5,903,099 A | 5/1999 | Johnson et al. | |
| 5,938,697 A | 8/1999 | Killion et al. | |
| 5,941,249 A | 8/1999 | Maynard | |
| 5,957,929 A | 9/1999 | Brenneman | |
| 5,984,963 A | 11/1999 | Ryan et al. | |
| 6,007,573 A | 12/1999 | Wallace et al. | |
| 6,015,431 A | 1/2000 | Thornton et al. | |
| 6,015,433 A | 1/2000 | Roth | |
| 6,017,977 A | 1/2000 | Evans et al. | |
| 6,036,725 A | 3/2000 | Avellanet | |
| 6,043,451 A | 3/2000 | Julien et al. | |
| 6,048,622 A | 4/2000 | Hagood et al. | |
| 6,059,766 A | 5/2000 | Greff | |
| 6,077,298 A | 6/2000 | Tu et al. | |
| 6,096,175 A | 8/2000 | Roth | |
| 6,099,561 A * | 8/2000 | Alt | 623/1.44 |
| 6,107,004 A | 8/2000 | Donadio, III | |
| 6,120,535 A | 9/2000 | McDonald et al. | |
| 6,132,460 A | 10/2000 | Thompson | |
| 6,133,547 A | 10/2000 | Maynard | |
| 6,139,564 A | 10/2000 | Teoh | |
| 6,143,022 A * | 11/2000 | Shull et al. | 623/1.13 |
| 6,159,239 A | 12/2000 | Greenhalgh | |
| 6,174,330 B1 | 1/2001 | Stinson | |
| 6,190,404 B1 | 2/2001 | Palmaz et al. | |
| 6,206,911 B1 | 3/2001 | Milo | |
| 6,224,627 B1 | 5/2001 | Armstrong et al. | |
| 6,224,630 B1 | 5/2001 | Bao et al. | |
| 6,245,104 B1 | 6/2001 | Alt | |
| 6,254,628 B1 | 7/2001 | Wallace et al. | |
| 6,258,117 B1 | 7/2001 | Camrud et al. | |
| 6,290,720 B1 | 9/2001 | Khosravi et al. | |
| 6,303,100 B1 | 10/2001 | Ricci et al. | |
| 6,315,788 B1 | 11/2001 | Roby | |
| 6,315,794 B1 | 11/2001 | Richter | |
| 6,331,188 B1 * | 12/2001 | Lau et al. | 623/1.13 |
| 6,355,055 B1 | 3/2002 | Waksman et al. | |
| 6,379,383 B1 | 4/2002 | Palmaz et al. | |
| 6,398,803 B1 | 6/2002 | Layne et al. | |
| 6,406,487 B2 | 6/2002 | Brenneman | |
| 6,406,490 B1 | 6/2002 | Roth | |
| 6,409,749 B1 | 6/2002 | Maynard | |
| 6,428,569 B1 | 8/2002 | Brown | |
| 6,447,478 B1 | 9/2002 | Maynard | |
| 6,454,738 B1 | 9/2002 | Tran et al. | |
| 6,458,152 B1 | 10/2002 | Khosravi et al. | |
| 6,458,153 B1 | 10/2002 | Bailey et al. | |
| 6,471,980 B2 | 10/2002 | Sirhan et al. | |
| 6,485,510 B1 | 11/2002 | Camrud et al. | |
| 6,506,211 B1 | 1/2003 | Skubitz et al. | |
| 6,520,984 B1 | 2/2003 | Garrison et al. | |
| 6,527,919 B1 | 3/2003 | Roth | |
| 6,533,905 B2 | 3/2003 | Johnson et al. | |
| 6,537,310 B1 | 3/2003 | Palmaz et al. | |
| 6,605,111 B2 | 8/2003 | Bose et al. | |
| 6,614,570 B2 | 9/2003 | Johnson et al. | |
| 6,618,921 B1 | 9/2003 | Thornton | |
| 6,620,192 B1 | 9/2003 | Jalisi | |
| 6,620,634 B2 | 9/2003 | Johnson et al. | |
| 6,624,730 B2 | 9/2003 | Johnson et al. | |
| 6,629,993 B2 | 10/2003 | Voinov | |
| 6,632,240 B2 | 10/2003 | Khosravi et al. | |
| 6,638,301 B1 * | 10/2003 | Chandrasekaran et al. | 623/1.34 |
| 6,666,882 B1 | 12/2003 | Bose et al. | |
| 6,669,719 B2 | 12/2003 | Wallace et al. | |
| 6,669,721 B1 | 12/2003 | Bose et al. | |
| 6,669,795 B2 | 12/2003 | Johnson et al. | |
| 6,673,102 B1 | 1/2004 | Vonesh et al. | |
| 6,676,987 B2 | 1/2004 | Zhong et al. | |
| 6,695,865 B2 | 2/2004 | Boyle et al. | |
| 6,699,278 B2 | 3/2004 | Fischell et al. | |
| 6,699,279 B2 | 3/2004 | Stevens et al. | |
| 6,746,478 B2 | 6/2004 | Jayaraman | |
| 6,752,826 B2 | 6/2004 | Holloway et al. | |
| 6,767,418 B1 | 7/2004 | Zhang et al. | |
| 6,776,795 B2 | 8/2004 | Pelton | |
| 6,820,676 B2 | 11/2004 | Palmaz et al. | |
| 6,849,085 B2 | 2/2005 | Marton | |
| 6,936,066 B2 | 8/2005 | Palmaz et al. | |
| 6,953,560 B1 | 10/2005 | Castro et al. | |
| 7,105,018 B1 | 9/2006 | Yip et al. | |
| 7,279,175 B2 | 10/2007 | Chen et al. | |
| 7,335,426 B2 * | 2/2008 | Marton et al. | 428/544 |
| 7,410,497 B2 | 8/2008 | Hastings et al. | |
| 7,947,071 B2 | 5/2011 | Schmid et al. | |
| 2001/0001834 A1 | 5/2001 | Palmaz et al. | |
| 2001/0032013 A1 * | 10/2001 | Marton | 623/1.15 |
| 2001/0039449 A1 | 11/2001 | Johnson et al. | |
| 2001/0044647 A1 | 11/2001 | Pinchuk et al. | |
| 2002/0007958 A1 | 1/2002 | Rivelli et al. | |
| 2002/0017503 A1 | 2/2002 | Banas et al. | |
| 2002/0019662 A1 | 2/2002 | Brauckman et al. | |
| 2002/0035774 A1 | 3/2002 | Austin | |
| 2002/0042645 A1 | 4/2002 | Shannon | |
| 2002/0046783 A1 | 4/2002 | Johnson et al. | |
| 2002/0142119 A1 | 10/2002 | Seward et al. | |
| 2002/0151965 A1 | 10/2002 | Roth | |
| 2002/0161342 A1 | 10/2002 | Rivelli, Jr. et al. | |
| 2002/0162605 A1 | 11/2002 | Horton et al. | |
| 2002/0165576 A1 | 11/2002 | Boyle et al. | |
| 2002/0165600 A1 | 11/2002 | Banas et al. | |
| 2002/0173809 A1 | 11/2002 | Fleischman et al. | |
| 2002/0187288 A1 | 12/2002 | Lim et al. | |
| 2002/0193869 A1 | 12/2002 | Dang | |
| 2002/0195579 A1 | 12/2002 | Johnson | |
| 2002/0198584 A1 | 12/2002 | Unsworth et al. | |
| 2003/0002994 A1 | 1/2003 | Johnson et al. | |
| 2003/0004567 A1 | 1/2003 | Boyle et al. | |
| 2003/0018354 A1 | 1/2003 | Roth et al. | |
| 2003/0023303 A1 * | 1/2003 | Palmaz et al. | 623/2.18 |
| 2003/0040791 A1 | 2/2003 | Oktay | |
| 2003/0050691 A1 | 3/2003 | Shifrin et al. | |
| 2003/0059640 A1 | 3/2003 | Marton et al. | |
| 2003/0060782 A1 | 3/2003 | Bose et al. | |
| 2003/0074049 A1 | 4/2003 | Hoganson et al. | |
| 2003/0078649 A1 | 4/2003 | Camrud et al. | |
| 2003/0083731 A1 | 5/2003 | Kramer et al. | |
| 2003/0127318 A1 | 7/2003 | Johnson et al. | |

(56) References Cited

U.S. PATENT DOCUMENTS

| | | | |
|---|---|---|---|
| 2003/0130718 A1* | 7/2003 | Palmas et al. ............... | 623/1.12 |
| 2003/0130721 A1 | 7/2003 | Martin et al. | |
| 2003/0139797 A1 | 7/2003 | Johnson et al. | |
| 2003/0153971 A1 | 8/2003 | Chandrasekaran | |
| 2003/0159920 A1 | 8/2003 | Roth | |
| 2003/0185895 A1 | 10/2003 | Lanphere et al. | |
| 2003/0187495 A1 | 10/2003 | Cully et al. | |
| 2003/0212430 A1 | 11/2003 | Bose et al. | |
| 2004/0006381 A1 | 1/2004 | Sequin et al. | |
| 2004/0014253 A1 | 1/2004 | Gupta et al. | |
| 2004/0030377 A1 | 2/2004 | Dubson et al. | |
| 2004/0034408 A1 | 2/2004 | Majercak et al. | |
| 2004/0054399 A1 | 3/2004 | Roth | |
| 2004/0054406 A1 | 3/2004 | Dubson et al. | |
| 2004/0059410 A1 | 3/2004 | Cox | |
| 2004/0098095 A1 | 5/2004 | Burnside et al. | |
| 2004/0106980 A1* | 6/2004 | Solovay et al. ............... | 623/1.13 |
| 2004/0107004 A1 | 6/2004 | Levine et al. | |
| 2004/0143317 A1 | 7/2004 | Stinson et al. | |
| 2004/0199239 A1 | 10/2004 | Austin et al. | |
| 2004/0225350 A1 | 11/2004 | Shanley | |
| 2004/0254520 A1 | 12/2004 | Porteous et al. | |
| 2005/0004653 A1 | 1/2005 | Gerberding et al. | |
| 2005/0010275 A1 | 1/2005 | Sahatjian et al. | |
| 2005/0033399 A1 | 2/2005 | Richter | |
| 2005/0165468 A1 | 7/2005 | Marton | |
| 2005/0165469 A1 | 7/2005 | Hogendijk | |
| 2005/0197687 A1 | 9/2005 | Molaei et al. | |
| 2005/0197689 A1 | 9/2005 | Molaei | |
| 2005/0197690 A1 | 9/2005 | Molaei et al. | |
| 2006/0069428 A1 | 3/2006 | Feller | |
| 2006/0100659 A1 | 5/2006 | Dinh et al. | |
| 2006/0115514 A1 | 6/2006 | Gengrinovitch | |
| 2006/0122691 A1 | 6/2006 | Richter | |
| 2006/0142838 A1 | 6/2006 | Molaei et al. | |
| 2006/0142842 A1 | 6/2006 | Molaei et al. | |
| 2006/0142845 A1 | 6/2006 | Molaei et al. | |
| 2006/0147492 A1 | 7/2006 | Hunter et al. | |
| 2006/0184231 A1 | 8/2006 | Rucker | |
| 2006/0259131 A1 | 11/2006 | Molaei et al. | |
| 2006/0271158 A1 | 11/2006 | Olson | |
| 2007/0016283 A1 | 1/2007 | Greenhalgh et al. | |
| 2007/0073385 A1 | 3/2007 | Schaeffer et al. | |
| 2007/0112411 A1 | 5/2007 | Obermiller et al. | |
| 2007/0250156 A1 | 10/2007 | Palmaz | |
| 2008/0027388 A1 | 1/2008 | Banas et al. | |
| 2008/0221665 A1 | 9/2008 | Peckham et al. | |
| 2009/0132022 A1 | 5/2009 | Banas | |
| 2009/0187240 A1 | 7/2009 | Clerc et al. | |
| 2010/0030320 A1 | 2/2010 | Feller, III | |
| 2011/0054590 A1 | 3/2011 | Leopold et al. | |

FOREIGN PATENT DOCUMENTS

| | | |
|---|---|---|
| EP | 1 604 697 | 12/2005 |
| GB | 2 125 442 A | 3/1994 |
| JP | 2003-102849 | 8/2003 |
| JP | 2007/502069 | 9/2007 |
| JP | 2007/526098 | 9/2007 |
| JP | 2007/526099 | 9/2007 |
| WO | WO 96/06814 | 3/1996 |
| WO | WO 98/53362 | 11/1998 |
| WO | WO 99/02092 | 1/1999 |
| WO | WO 99/60267 | 12/1999 |
| WO | WO 99/62432 | 12/1999 |
| WO | WO 00/62711 | 10/2000 |
| WO | WO 01/21097 | 3/2001 |
| WO | WO 01/53559 | 7/2001 |
| WO | WO 01/87371 | 11/2001 |
| WO | WO 01/89420 | 11/2001 |
| WO | WO 01/91823 | 12/2001 |
| WO | WO 01/95697 | 12/2001 |
| WO | WO 02/34163 | 5/2002 |
| WO | WO 02/38080 | 5/2002 |
| WO | WO 02/38086 | 5/2002 |
| WO | WO 02/060506 | 8/2002 |
| WO | WO 03/003943 | 1/2003 |
| WO | WO 03/011363 | 2/2003 |
| WO | WO 03/013337 | 2/2003 |
| WO | WO 03/015840 | 2/2003 |
| WO | WO 03/018100 | 3/2003 |
| WO | WO 03/075793 | 9/2003 |
| WO | WO 03/075799 A1 | 9/2003 |
| WO | 03/099161 A2 | 12/2003 |
| WO | WO 2004/002370 A1 | 1/2004 |
| WO | WO 2004/008504 | 1/2004 |
| WO | WO 2004/028340 | 4/2004 |
| WO | 2005/084583 | 9/2005 |
| WO | 2005/084584 | 9/2005 |
| WO | 2005/084585 | 9/2005 |
| WO | 2006/125022 | 4/2006 |
| WO | 2006/071215 | 7/2006 |
| WO | 2006/071242 | 7/2006 |
| WO | 2006/071243 | 7/2006 |
| WO | 2006/071244 | 7/2006 |
| WO | 2006/071245 | 7/2006 |

OTHER PUBLICATIONS

Dieter, George, *Mechanical Metallurgy*, Singapore, McGraw-Hill Book Co., 10$^{th}$ Printing 1984, pp. 111-117, 142-145, and 234-237. TA405.D53.

Freiherr, Greg, "Shape-Memory Alloys Offer Untapped", Medical Device & Diagnostic Industry Magazine, Mar. 1998, 5 pages [retrieved on Jun. 30, 2004].

Fu et al., "TiNi-based thin films in MEMS applications: a review", Sensors and Actuators, Article in Press, Elsevier, Feb. 2004, 14 pages.

Gertner et al., "Drug Delivery from Electrochemically Deposited Thin Metal Films", Electrochemical and Sold-State Letter, 6 (4) J4-J6, 2003.

Gertner et al., "Electrochemistry and Medical Devices: Friend or Foe?", The Electrochemical Society Interface, Fall 2003, pp. 20-24.

Gupta et al., "Nitinol Thin Film Three-Dimensional Devices—Fabrication and Applications", http://www.tinialloy.com/pdf/smst.pdf, Sep. 7, 2003 [retrieved Dec. 1, 2004].

He et al., "$CO_2$ laser annealing of sputtering deposited NiTi shape memory thin films", Journal of Micromechanics and Microengineering, May 20, 2004, pp. 950-956.

Kaczmarek, S. M., "Pulsed laser deposition—today and tomorrow", STL'96, Proc. SPIE, vol. 3187, 1997, pp. 129-134.

Krebs et al., "Pulsed Laser Deposition (PLD)—a Versatile Thin Film Technique", Advances in Solid State Physics 2003, 43, 505-517.

Nakayama et al., "Fabrication of micropored elastomeric film-covered stents and acute-phase performances", Journal of Biomedical Mateirals Research Part A, vol. 64A, Issue 1, Sep. 30, 2002, pp. 52-61.

Neocera, Inc. Brochure—Pulsed Laser Deposition, www.neocera.com [retrieved Dec. 1, 2004].

Pelleiter et al., "Effect of high energy argon implantation into NiTi shape memory alloy", Surface and Coatings Technology, 158-159, 2002, pp. 301-308.

Padhi et al., "Planarization of Copper Thin Films by Electropolishing in Phosphoric Acid for ULSI Application", Journal of Electrochemical Society, vol. 150, 2003, pp. G10-G14.

Ren et al., "Carbon nitride materials synthesized by Ion-assisted pulsed laser deposition", RIKEN Review No. 43, Jan. 2002, pp. 41-44.

Schetky et al., "Issues in the Further Development of Nitinol Properties and Processing for Medical Device Application", Proceedings, ASM Materials & Processes for Medical Devices Conference, Anaheim, in press, 2003, 6 pages.

Shabalovskaya et al., "Comparative performances of Nitinol surfaces in protein adsorption and platelet adhesion—Preliminary results", Institute for Physical Research and Technology, Ames Laboratory, Ames, IA University of Washington, Seattle WA Memry Corporation, Bethel CT, 2004, 10 pages.

Stoeckel et al., "A survey of stent designs", Min Invas Ther & Allied Technol, 11(4), 2002, pp. 137-147.

(56) References Cited

OTHER PUBLICATIONS

International Search Report for PCT Application No. PCT/US2005/006993.
International Search Report for PCT Application No. PCT/US2005/007161.
International Search Report for PCT Application No. PCT/US2005/007173.
International Search Report for PCT Application No. PCT/US2005/006895.
International Search Report from European Application No. PCT/US2005/007282 mailed Jul. 5, 2005, 15 pages.
International Search Report from European Application No. PCT/US2005/007164 mailed Jul. 5, 2005, 13 pages.
International Search Report from European Application No. PCT/US2006/019126 mailed Feb. 1, 2007, 16 pages.

* cited by examiner

MEDICAL DEVICES INCLUDING METALLIC FILMS

FIELD OF THE INVENTION

The invention relates to medical devices, such as endoprostheses, and methods of making the devices.

BACKGROUND

The body includes various passageways such as arteries, other blood vessels, and other body lumens. These passageways sometimes become occluded or weakened. For example, the passageways can be occluded by a tumor, restricted by plaque, or weakened by an aneurysm. When this occurs, the passageway can be reopened or reinforced, or even replaced, with a medical endoprosthesis. An endoprosthesis is typically a tubular member that is placed in a lumen in the body. Endoprostheses can be delivered inside the body by a catheter that supports the endoprosthesis in a compacted or reduced-size form as the endoprosthesis is transported to a desired site. Upon reaching the site, the endoprosthesis is expanded, for example, so that it can contact the walls of the lumen.

The expansion mechanism may include forcing the endoprosthesis to expand radially. For example, the expansion mechanism can include the catheter carrying a balloon, which carries a balloon-expandable endoprosthesis. The balloon can be inflated to deform and to fix the expanded endoprosthesis at a predetermined position in contact with the lumen wall. The balloon can then be deflated, and the catheter withdrawn.

In another delivery technique, the endoprosthesis is formed of an elastic material that can be reversibly compacted and expanded, e.g., elastically or through a material phase transition. During introduction into the body, the endoprosthesis is restrained in a radially compacted condition. Upon reaching the desired implantation site, the restraint is removed, for example, by retracting a restraining device such as an outer sheath, enabling the endoprosthesis to self-expand by its own internal elastic restoring force.

SUMMARY OF THE INVENTION

The invention relates to medical devices, such as endoprostheses, and methods of making the devices. Exemplary endoprostheses include stents, covered stents, and stent-grafts.

In some embodiments, an endoprosthesis for deployment within a body passage includes a tubular framework and a metallic film having a thickness of about 50 µm or less and disposed internally of the tubular framework. The endoprosthesis may be self-expanding.

The tubular framework may have an internal surface. The metallic film, which may be generally tubular in shape, may have an outer surface that contacts the internal surface of the tubular framework.

The film may be a deposited metallic film including, e.g., deposited nickel and titanium. The deposited film may have a thickness of about 50 µm or less, 50 µm or less, e.g., about 35 µm or less. The deposited film may have a thickness of 4 µm or greater. The film may exhibit super-elastic properties. In embodiments, the film is not shape set.

The endoprosthesis, when in a deployed state within a body passage, may exert an outward radial force against the body passage, with essentially all of the outward radial force resulting from the tubular framework.

The endoprosthesis may have an internal surface that is substantially defined by an internal surface of the metallic film.

In embodiments, the endoprosthesis includes only one framework.

In some embodiments, the endoprosthesis includes at least a second tubular framework. At least a portion or all of the metallic film is sandwiched between the tubular framework and the second tubular framework. The endoprosthesis may be self expanding. In embodiments, neither the tubular framework nor the second tubular framework, by itself, exerts a radial force sufficient to secure the endoprosthesis within a body passage but together, the tubular framework and second tubular framework exert force sufficient to secure the endoprosthesis. In a deployed state, the tubular framework and the second tubular framework may each exert a radial force. The radial force of the second tubular framework may be greater than the radial force of the tubular framework.

A total radial thickness of the tubular framework and the second tubular framework may be about 75 microns or less. The tubular framework and the second tubular framework may have at least some relative freedom of movement along at least one of the radial, circumferential, and longitudinal dimensions.

Substantially all or all of the metallic film may be a single layer.

In some embodiments, a self-expanding endoprosthesis for deployment within a body passage includes a first tubular framework, a tubular member disposed around the first tubular framework, and a second tubular framework disposed around the tubular member.

In embodiments, neither of the first and second tubular frameworks alone exerts sufficient outward radial force to self-expand the endoprosthesis within a body passage but the first and second tubular frameworks together exert sufficient outward radial force to self-expand the endoprosthesis.

The film may be a deposited metallic film including, e.g., deposited nickel and titanium. The deposited film may have a thickness of about 50 µm or less, 50 µm or less, e.g., about 35 µm or less. The deposited film may have a thickness of 4 µm or greater. The film may exhibit super-elastic properties. In embodiments, the film is not shape set.

In embodiments, a delivery device for deploying an endoprosthesis within a body passage includes an elongate inner member, a self-expanding endoprosthesis disposed about a distal portion of the inner member, the endoprosthesis comprising a tubular framework disposed about a deposited metallic film and an outer sheath surrounding the elongate inner member and the self-expanding endoprosthesis, wherein the tubular framework prevents substantial frictional contact between the tubular member and the outer sheath.

In one aspect, the invention features an endoprosthesis including a metallic film, e.g., a vapor deposited film, including nickel, titanium, and chromium. A ratio of a weight of chromium of the metallic film to a combined weight of nickel, titanium, and chromium of the metallic film is at least 0.001 and can be less than 0.0075.

Other aspects, features, and advantages of the invention will be apparent from the description of the preferred embodiments thereof and from the claims.

DETAILED DESCRIPTION

Figure 1:
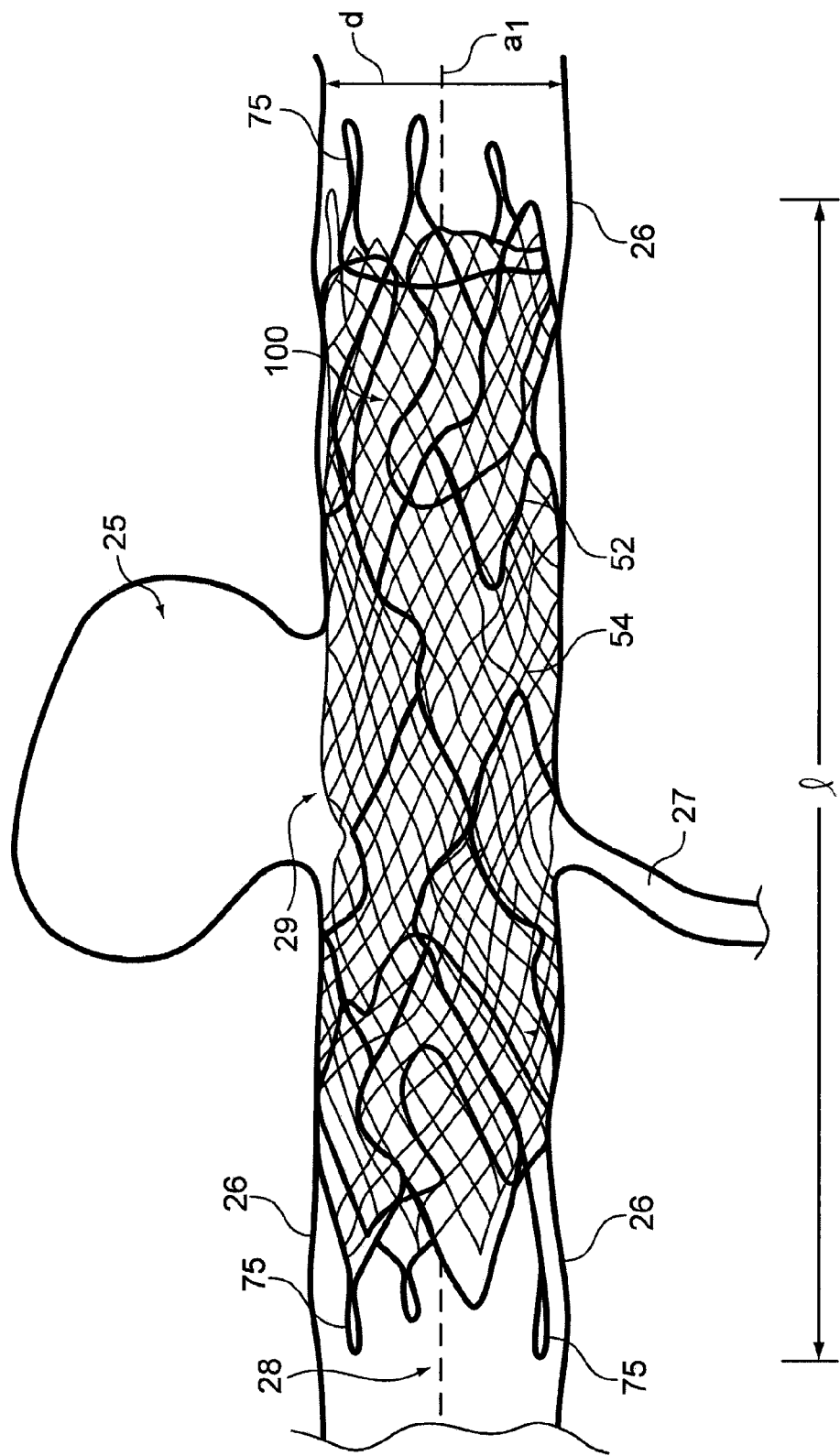
FIG. 1 is a side view of an endoprosthesis in the radially expanded state as deployed within a body passage adjacent an aneurysm.

Referring to FIG. 1, an endoprosthesis 100 is deployed within a body passage, e.g., within a vessel weakened by an aneurysm, e.g., an aneurysm 25 of a vessel 26 of a human brain. Endoprosthesis 100 includes a framework, e.g., a stent body 52, covered by a tubular member or cover 54, made of thin metallic film. The stent body provides a relatively rigid framework that secures the endoprosthesis at the treatment site. The framework defines relatively large openings or fenestrations that contribute to the mechanical properties of the stent. The cover 54 is relatively thin and flexible and includes smaller fenestrations that contribute to the mechanical properties of the cover and can occlude the fenestrations of the stent.

In some embodiments, endoprosthesis 100 modifies an amount or velocity of blood passing between vessel 26 and aneurysm 25. For example, prosthesis 100 can be deployed to reduce or block blood flow between vessel 26 and aneurysm 25, e.g., to occlude the aneurysm 25. If so deployed, prosthesis 100 may sufficiently reduce blood flow to allow clotting or other healing processes to take place within aneurysm 25 and/or opening 29 thereof. Tubular member 54 can provide a greater attenuation of the blood flow into the aneurysm 25 than stent body 52 alone. Endoprosthesis 100, however, can allow some flow to pass between vessel 26 and aneurysm 25 even while providing some reduction in the rate and/or volume of flow. Prosthesis 100 can also (or alternatively) allow blood to pass between vessel 26 containing the prosthesis and adjacent vessels, e.g., feeder vessel 27, while still providing reduced flow with respect to the aneurysm.

Figure 2A:
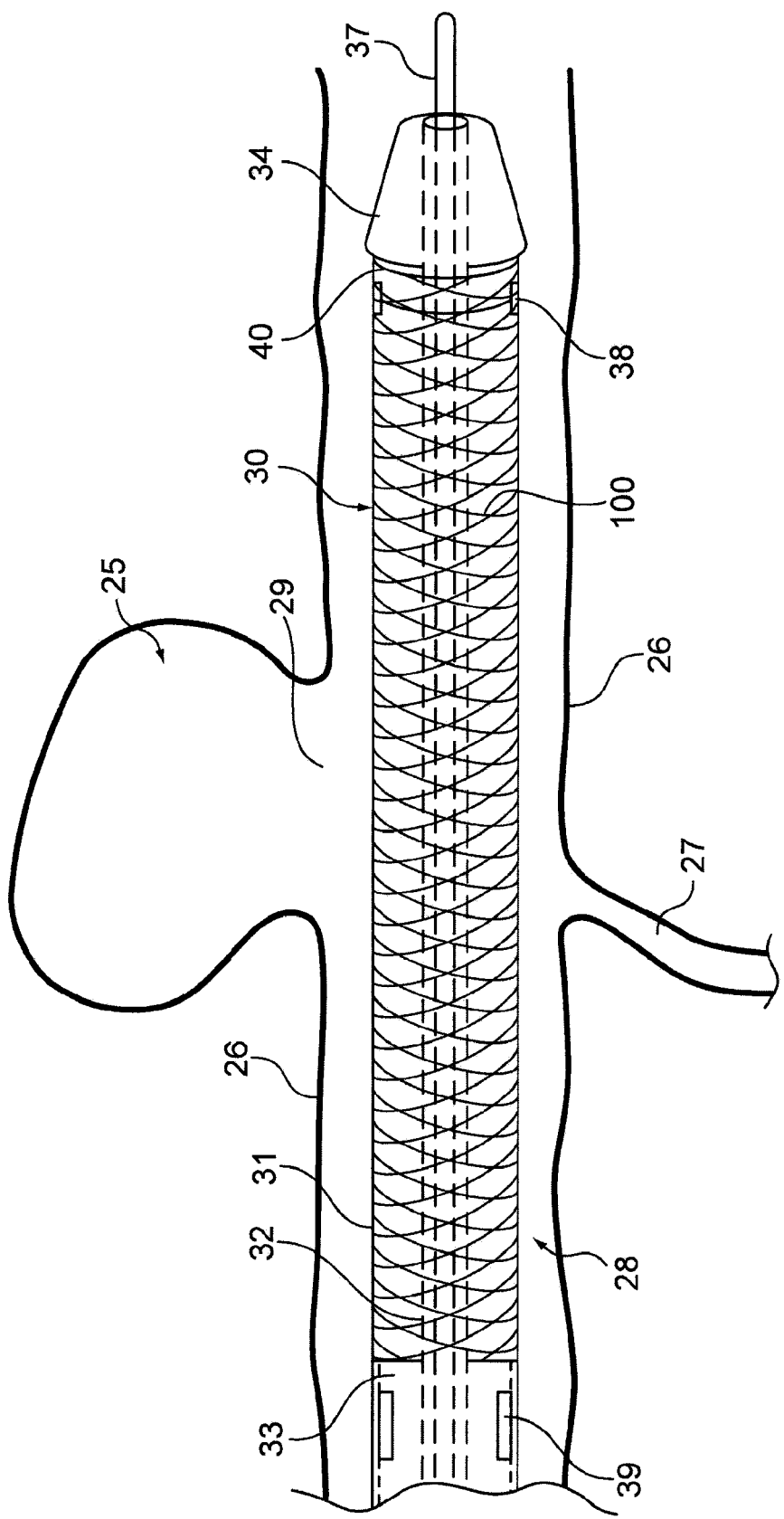
FIG. 2a is a side view of a distal portion of a deployment device prior to radial expansion of the endoprosthesis.

Referring to FIG. 2a, endoprosthesis 100 is deployed to aneurysm 25 using a deployment device 30, which includes a retractable outer sheath 31 and an inner catheter 32. FIG. 2a shows only a distal portion of the delivery device. An operator manipulates the device 30 using a proximal portion (not shown). Device 30 is introduced over a guide wire 37 extending along an interior 28 of vessel 26. During introduction, the endoprosthesis 100 is radially compacted between outer sheath 31 and inner catheter 32 adjacent a distal end 40 of the outer sheath. Endoprosthesis 100 is longitudinally restrained by a proximal stop 33 and a distal tip 34 of inner catheter 32. Device 30 includes distal and proximal markers 38,39, which can be radiographically monitored to determine when endoprosthesis 100 has reached aneurysm 25. Prosthesis 100 includes markers 75 (FIG. 1), to provide radiopacity, which can also or alternatively be used to visualize the position of endoprosthesis 100.

Figure 2B:
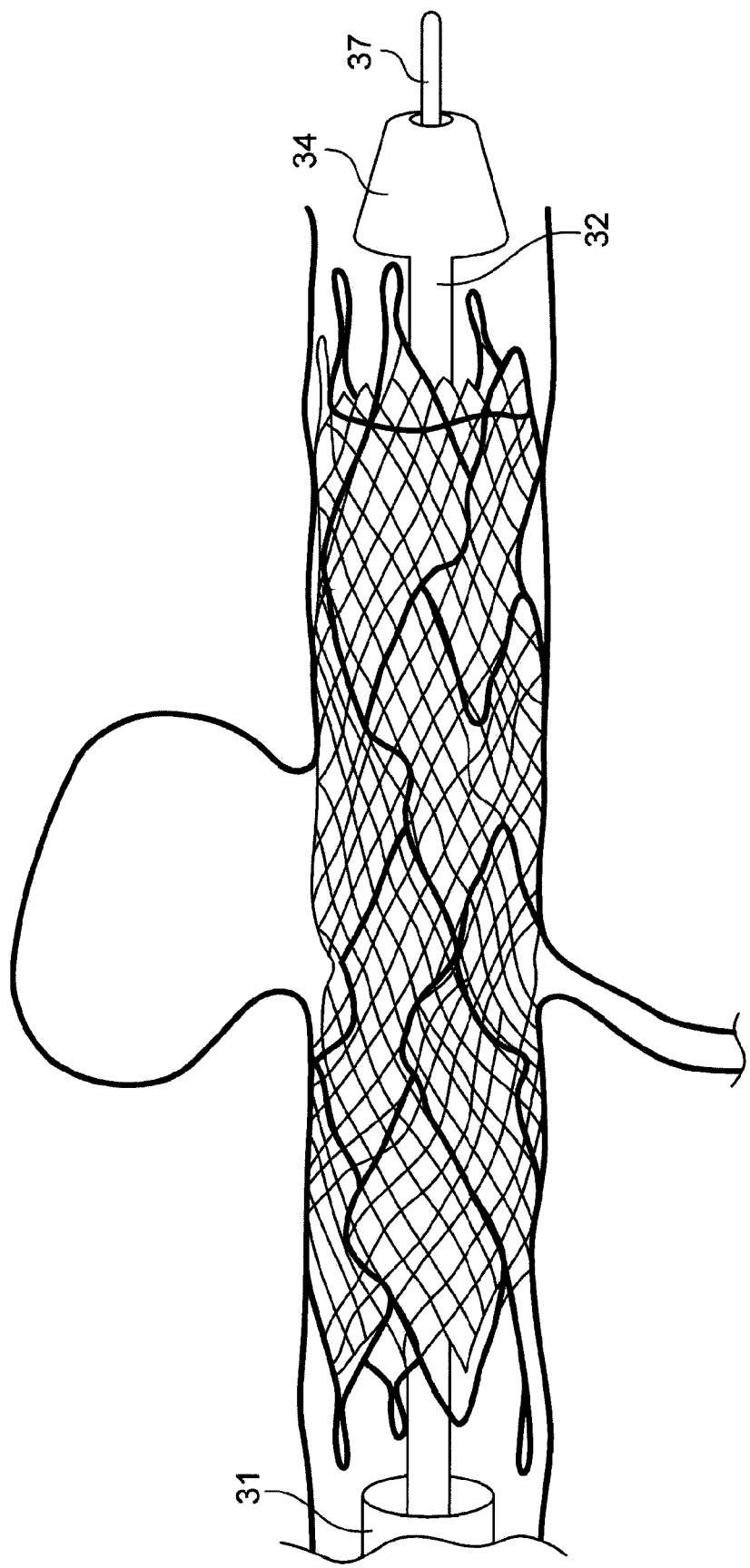
FIG. 2b is a side view of the distal portion of the deployment device subsequent to radial expansion of the endoprosthesis adjacent the aneurysm.

With reference to FIG. 2b, the outer sheath 31 is retracted upon reaching the desired deployment site, e.g., aneurysm 25. In some embodiments, endoprosthesis 100 self-expands by its own internal elastic restoring force when the radially restraining outer sheath is retracted. Alternatively, or in combination with self-expansion, deployment of prosthesis 100 may include use of a balloon or other device to radially expand prosthesis 100 within vessel 26. The inner catheter 32 and guide wire 37 are withdrawn from vessel 26. Suitable delivery systems include the Neuroform, Neuroform2, and Wingspan Stent System available from Boston Scientific Target Therapeutics, Fremont, Calif. In embodiments, the outer sheath and/or inner catheter includes a reinforcing member to respectively resist elongation or compression as the outer sheath is withdrawn. Such reinforcing members include polymer shafts, braids, and coil structures. Endoprosthesis 100 can be deployed using a guidewireless deployment device.

Upon expansion, endoprosthesis 100 assumes a shape and radial extent generally coextensive with an inner surface of the vessel 26, e.g., a tubular shape centered about a longitudinal axis $a_1$ of the prosthesis (FIG. 1). Depending upon the application, prosthesis 100 can have a diameter d of between, for example, 1 mm to 46 mm. In certain embodiments, a prosthesis for deployment within a vessel at an aneurysm can have an expanded diameter d of from about 2 mm to about 6 mm, e.g., about 2.5 mm to about 4.5 mm. Depending upon the application, prosthesis 100 can have a length along axis $a_1$ of at least 5 mm, at least 10 mm, e.g., at least about 30 mm. An exemplary embodiment has an expanded diameter of about 3.5 mm and a length of about 15 mm. In embodiments, the stent body has a closed cell framework, an open cell framework, a helical framework, a braided framework, or combination thereof.

In some embodiments the tubular member 54 of endoprosthesis 100 includes a metallic film deposited by a vapor deposition process. Vapor deposited materials are formed by depositing film constituents from a vapor or a vacuum onto a surface. In embodiments, the constituents are vaporized by bombarding, heating or sputtering a bulk target. The vaporized constituents deposit on a substrate to form the film. Deposited films can exhibit highly uniform thickness and microstructure in very thin films, e.g. about 50 microns or less, e.g. 4-35 microns. Suitable vapor deposition processes are described in Busch et al. U.S. Pat. No. 5,061,914, Bose et al. U.S. Pat. No. 6,605,111, Johnston U.S. Pat. No. 6,533,905, and Gupta et al. U.S. 2004/0014253, the entire contents of all of which are hereby incorporated by reference.

In some embodiments, the deposited film can include an alloy of nickel and titanium present in amounts sufficient to provide the deposited film with desirable mechanical or shape memory properties. For example, the film may include an alloy, e.g., a superelastic or pseudo-elastic metal alloy, as described, for example, in Schetsky, L. McDonald, "Shape Memory Alloys," Encyclopedia of Chemical Technology (3rd ed.), John Wiley & Sons, 1982, vol. 20. pp. 726-736; and commonly assigned U.S. Ser. No. 10/346,487, filed Jan. 17, 2003. The alloy may be nitinol. The alloy may include a third compound, e.g., chromium, which modifies a mechanical property, e.g., a hardness or elasticity, of the film. Tubular member 54 may include a deposited metal film including nickel, titanium, and, optionally, chromium. Exemplary films and deposition of such films is described in U.S. application Ser. No. 11/025,860, filed concurrently herewith, titled MEDICAL DEVICES INCLUDING METALLIC FILMS AND METHODS FOR MAKING SAME, which application is incorporated herein by reference.

Figure 3:
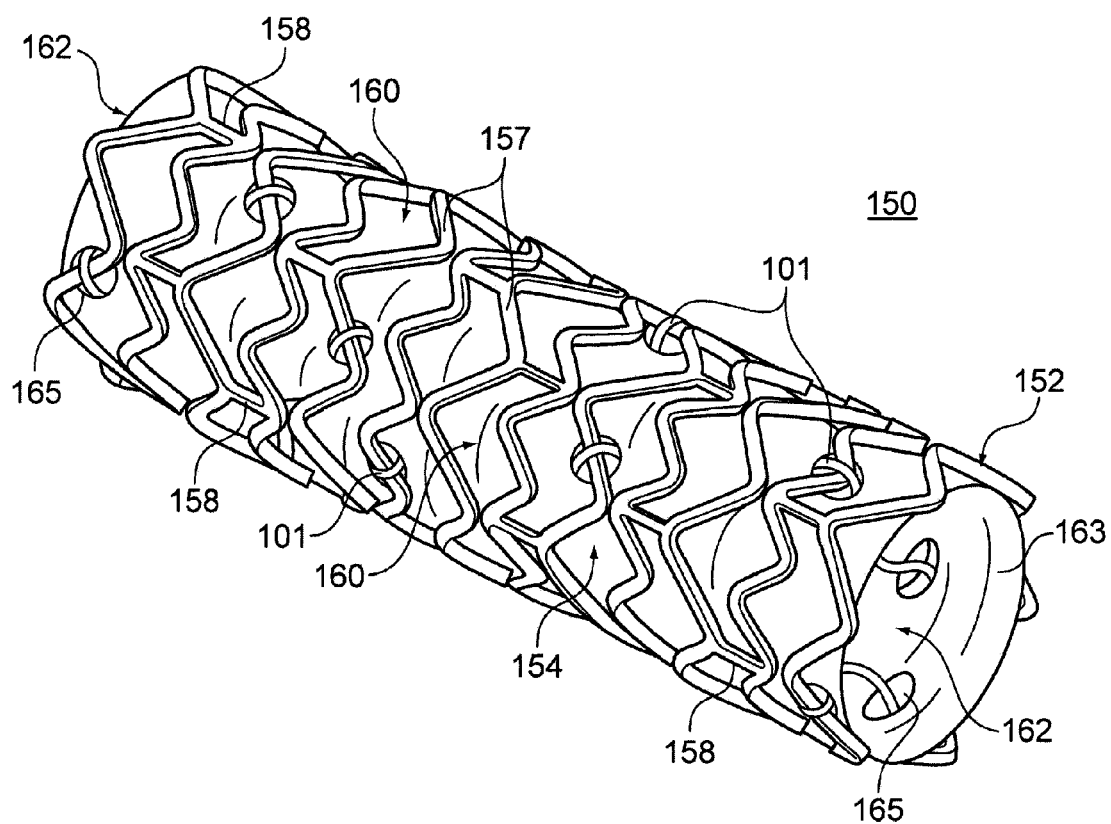
FIG. 3 is a perspective view of an endoprosthesis.

Referring to FIG. 3, an endoprosthesis 150 includes a framework, e.g., stent body 152, and a tubular member 154 disposed internally of stent body 152. Stent body 152 is defined by a plurality of circumferential bands 157 connected by longitudinal members 158 and defining fenestrations 160 therebetween. Tubular member 154 may be a deposited metallic film. Although not shown in FIG. 3, tubular member 154 may define a plurality of fenestrations, e.g., as discussed for tubular member 54 (FIG. 1). Because tubular member 154 is disposed internally of stent body 152, an interior 162 of endoprosthesis 150 is defined by a surface 163 of tubular member 154 and presents a generally smoother topography, e.g., with fewer projections, than if stent body 152 were internal of the tubular member.

During introduction via a delivery device along a body passageway, e.g., within a blood vessel, stent body 152 is positioned between the surrounding delivery device, e.g., the outer sheath 31 of device 30, and the tubular member 154. Upon deployment, as the outer sheath is retracted over the endoprosthesis, the substantially all or all of any friction between the sheath and endoprosthesis is experienced by the stent body 152 not the tubular member 154. For example, at least about 75% or at least 90% of the frictional contact between the sheath and the endoprosthesis during radial expansion may be between an inner surface of the outer sheath and the tubular framework. Such a configuration can protect the tubular member from damage, e.g., tears, when the endoprosthesis is loaded into the delivery device and during deployment.

As the endoprosthesis 150 radially expands against a body passageway, stent body 152 can limit or prevent contact between the internal surface of the body passageway and the tubular member. For example, locating the tubular member internal of the stent body prevents the stent body from forcing the tubular member against the body passageway during radial expansion. Hence, fenestrations of the tubular member, if present, will not slide with significant force against the body passageway internal surface so as to minimize mechanical damage from the fenestrations to the body passageway.

In embodiments, the endoprosthesis is a re-sheathable endoprosthesis, such as a closed cell stent body with internal tubular member.

Once deployed, tubular member 154 shields blood flowing longitudinally through the endoprosthesis from stent body 152, e.g., from circumferential bands 157 and longitudinal members 158. Hence, a tendency for the blood flow to be disrupted or perturbed by stent body 152 is reduced or eliminated. A tendency for blood to clot within the interior 162 is also reduced or eliminated because the generally smoother topography presented by tubular member 154 offers fewer projections than if stent body 152 were internal of tubular member 152.

Because stent body 152 is disposed of connected circumferential bands rather than a more contiguous surface, stent body 152 presents less surface area to the wall of the passageway than would tubular member 154. Consequently, when radially expanded against the wall of a body passageway, e.g., vessel 26, endoprosthesis 150 produces less metal to tissue contact than if the stent body 152 were not positioned between the passageway wall and the tubular member 154. Additionally, interstices created by stent body 152 between the passageway wall and tubular member 154 can enhance endothelial growth and recovery.

Endoprosthesis 150 can be assembled by overexpanding stent body 152 to a greater diameter than it assumes in a body passageway and then sliding or drawing the tubular member into the interior of the stent body. Subsequently, stent body 152 is allowed to contract against the tubular member. In embodiments, when expanded within a body passageway, the tubular member is about as long as the stent body and may be shorter.

The tubular member and stent body can be secured, e.g., mechanically, with adhesive, or a combination thereof. As shown, filaments 101 pass around portions of stent body 152 and through fenestrations 165 of tubular member 154. Filaments 101 can be formed of a polymer, a suture, a ductile metal wire, such as nitinol or gold wire, or other suitable material. In some embodiments, the tubular member differs from a fabric at least in that the tubular member is a metallic film that lacks fibers that can be pushed apart to receive a filament as by sewing a fabric. Accordingly, the fenestrations can be formed prior to the process of passing the filament through the tubular member. Fenestrations that receive the filaments can be formed by, e.g., etching, laser cutting, or a photolithographic process. Other mechanical securing structures include fasteners, such as grommets and rivets. Securing techniques are described in U.S. Ser. No. 11/025,866, filed contemporaneously herewith and incorporated herein by reference.

In embodiments, substantially all of the radial outward force exerted by endoprosthesis 150 is due to stent body 152. In some embodiments, tubular member 154 is a deposited metallic film of a memory alloy that is shape set to a larger diameter than the radially expanded diameter of the stent body 152 within a body passageway. The resulting outward radial force exerted by the tubular member 154 against the stent body helps secure the tubular member and stent body. The tubular member outward force may supplement the outward force exerted by the stent body.

As shown in FIG. 3, the tubular member includes, along the radial dimension, only a single layer. In other embodiments, tubular member 154 itself, or endoprosthesis 150 as a whole, includes multiple tubular member layers, e.g., multiple deposited metallic film layers. For example, a second tubular member can be disposed external of stent body 152. In embodiments, the tubular member is a thin film of superelastic alloy and is not shape set.

Figure 4:
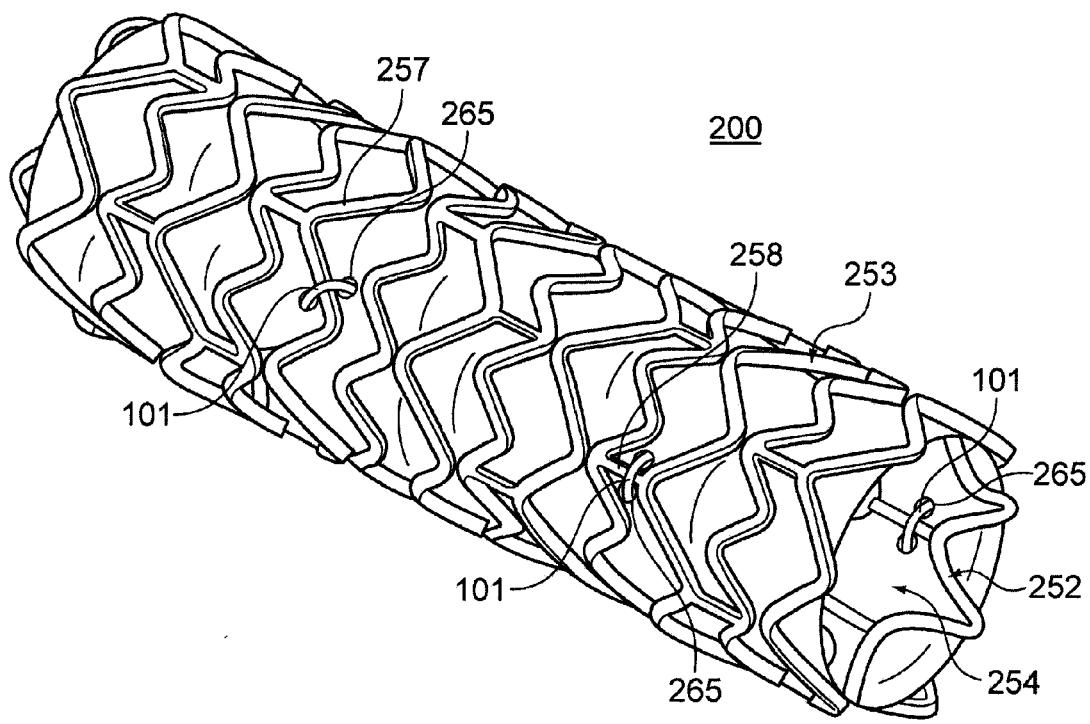
FIG. 4 is a perspective view of an endoprosthesis.

Referring to FIG. 4, an endoprosthesis 200 includes a tubular member 254 sandwiched between an internal stent body 252 and an external stent body 253. Each stent body 252, 253 alone may exert less outward radial force than required to maintain a position of the deployed endoprosthesis within a body passageway. Hence, each stent body 252, 253 alone may be more radially compliant than a single stent body that provides sufficient radial force to secure an endoprosthesis. When loading the endoprosthesis 200 into a deployment device, the compliant stent bodies tolerate radial compaction without damage. When deployed, however, stent bodies 252, 253 cooperate to exert sufficient outward radial force to maintain the endoprosthesis in position within a body lumen.

Either of stent bodies 252, 253 may exert a greater outward radial force than the other. In embodiments, internal stent body 252 exerts a greater radial outward force, which helps secure internal stent body 252 and tubular member 254 with respect to external stent body 253. In embodiments, a radial thickness of each stent body 252, 253 is about 60 µm or less, about 50 µm or less, about 30 µm or less, e.g., about 25 µm or less. The total radial thickness of stent bodies 252, 253 may be about 120 µm or less, about 100 µm or less, about 60 µm or less, e.g., about 50 µm or less. One of the stent bodies 252, 253 may make up at least about 50%, at least about 75%, e.g., at least about 85% of the total radial thickness.

In some embodiments, stent bodies 252, 253 and tubular member 254 are secured with respect to one another by filaments 101, which pass through fenestrations 265 of the tubular member and pass around and/or are secured to either or both of stent bodies 252, 253. In embodiments, a given filament secures the tubular member with respect to one but not both stent bodies 252, 253.

Endoprosthesis 200 can be configured so that stent bodies 252, 253 have relative freedom of movement with respect to one another and/or with respect to tubular member 254. The freedom of movement may be provided along a given dimension, e.g., a radial, a circumferential, a longitudinal dimension, or combination thereof. For example, filaments 101 may have a length sufficient to provide some freedom of movement. Filaments that pass around longitudinal members 258 can allow longitudinal movement whereas filaments that pass around portions of circumferential bands 257 can allow circumferential movement. In some embodiments, stent bodies 252, 253 have essentially no freedom of movement along one or more dimensions, e.g., along one or all of the radial, circumferential, and longitudinal dimensions. Securing techniques alternative to or supplemental to filaments can be used.

Figure 5:
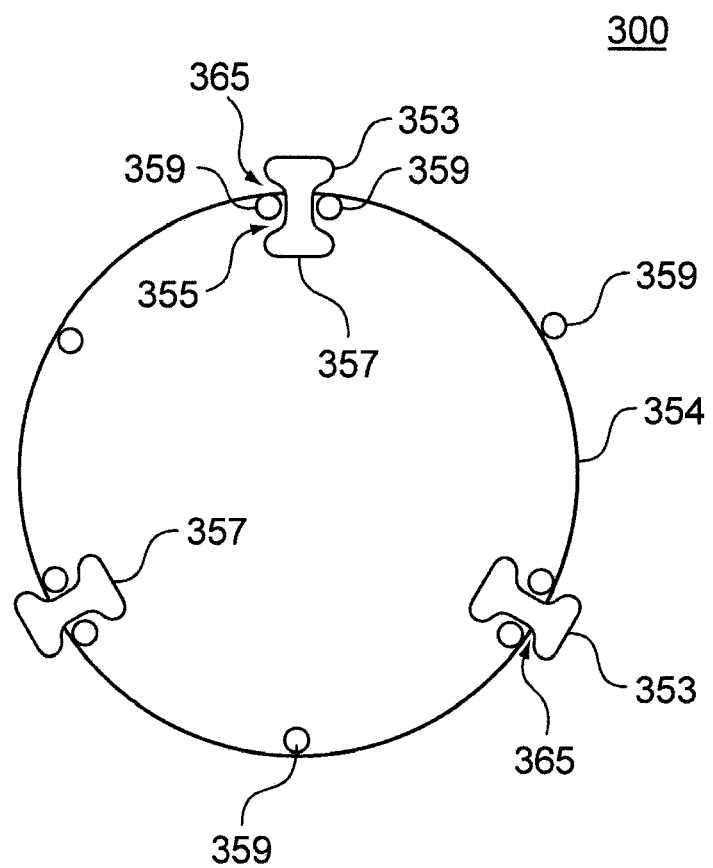
FIG. 5 is an end-on cross-sectional view of an endoprosthesis.

Referring to FIG. 5, an endoprosthesis 300 includes a tubular member 354 sandwiched between an internal stent body and an external stent body. One or both of the stent bodies of endoprosthesis 300 can be secured to the other via radially extending projections. As seen in FIG. 5, the external stent body includes projections 353, each extending through a fenestration 365 of tubular member 354 and engaging a portion of the internal stent body, e.g., an aperture 355. Apertures may or may not be closed and can be formed within a longitudinal member 359 or circumferential band of the stent body. The apertures are positioned to receive the projections when the two stent bodies mate.

An end 357 of each projection 353 can be flattened or otherwise broadened to prevent the projection from retracting through the aperture 355. Depending upon the relative shape and size of the apertures and projections, the apertures and projections can be configured to provide the stent bodies with radial, longitudinal and/or circumferential freedom of movement.

Other examples of endoprostheses including a thin film as well as related systems and methods are described in U.S. provisional patent application No. 60/549,287, filed Mar. 2, 2004, which application is incorporated herein by reference.

Methods and structures for securing a framework and one or more deposited thin film covers are described in U.S. patent application Ser. No. 11/025,866, titled MEDICAL DEVICES INCLUDING METALLIC FILMS AND METHODS FOR MAKING SAME, and filed concurrently herewith, which application is incorporated herein by reference.

An endoprosthesis may include features to enhance a flexibility of the endoprosthesis as described in U.S. patent application Ser. No. 11/025,158, titled MEDICAL DEVICES INCLUDING METALLIC FILMS AND METHODS FOR MAKING SAME, and filed concurrently herewith, which application is incorporated herein by reference.

An endoprosthesis may include a deposited thin film and a polymer as described in U.S. patent application Ser. No. 11/025,867, titled MEDICAL DEVICES INCLUDING METALLIC FILMS AND METHODS FOR MAKING SAME, and filed concurrently herewith, which application is incorporated herein by reference.

An endoprosthesis may include one or more filaments, e.g., wires, adapted to enhance mechanical properties of a deposited thin film as described in U.S. patent application Ser. No. 11/025,684, titled MEDICAL DEVICES INCLUDING METALLIC FILMS AND METHODS FOR MAKING SAME, and filed concurrently herewith, which application is incorporated herein by reference.

Methods for loading an endoprosthesis into a delivery device and systems for delivering an endoprosthesis to a treatment site are described in U.S. patent application Ser. No. 11/025,660, titled MEDICAL DEVICES INCLUDING METALLIC FILMS AND METHODS FOR LOADING AND DEPLOYING SAME, which application is incorporated herein by reference.

All publications, references, applications, and patents referred to herein are incorporated by reference in their entirety.

Other embodiments are within the claims.

What is claimed is:

1. An endoprosthesis for deployment within a body passage, comprising:
    a framework having fenestrations; and
    a tubular member having fenestrations that are smaller than the fenestrations in the framework, the tubular member comprising a metallic film having a thickness of about 50 µm or less, wherein the framework and the tubular member are secured to one another by a plurality of filaments that pass through the fenestrations, and can move relative to one another longitudinally, circumferentially and radially.

2. The endoprosthesis of claim 1, wherein the endoprosthesis is self-expandable.

3. The endoprosthesis of claim 1, wherein the metallic film comprises a super-elastic alloy of nickel and titanium.

4. The endoprosthesis of claim 1, wherein the endoprosthesis, when deployed within a body passage, exerts an outward radial force against the body passage, essentially all of the outward radial force resulting from the framework.

5. The endoprosthesis of claim 4, wherein the tubular member exerts an additional outward radial force against the body passage.

6. The endoprosthesis of claim 5, wherein the tubular member is a deposited metallic film of a memory alloy that is shape set to a larger diameter than the radially expanded diameter of the framework when deployed.

7. The endoprosthesis of claim 1, wherein the endoprosthesis has an internal surface, the internal surface substantially defined by an internal surface of the metallic film.

8. The endoprosthesis of claim 1, wherein the endoprosthesis comprises only one framework.

9. The endoprosthesis of claim 1, wherein substantially all of the metallic film is a single layer.

10. The endoprosthesis of claim 1, wherein the entire metallic film is a single layer.

11. The endoprosthesis of claim 1, wherein the framework comprises a plurality of circumferential bands connected by longitudinal members, thereby defining the fenestrations of the framework therebetween.

12. The endoprosthesis of claim 1, wherein the metallic film comprises a super-elastic metal alloy.

13. The endoprosthesis of claim 1, wherein the metallic film comprises an alloy of nickel and titanium.

14. The endoprosthesis of claim 13, wherein the alloy additionally comprises chromium.

15. The endoprosthesis of claim 1, wherein the tubular member consists of the metallic film.

16. The endoprosthesis of claim 1, wherein the tubular member is a deposited metallic film.

17. The endoprosthesis of claim 1, wherein the tubular member is a deposited metallic film of nitinol.

18. The endoprosthesis of claim 1, additionally comprising one or more radio-opacity markers.

19. The endoprosthesis of claim 1, wherein the tubular member comprises only a single layer along a radial dimension.

20. The endoprosthesis of claim 1, wherein the metallic film has a thickness of 4-35 µm.

* * * * *